US012685431B2

(12) United States Patent
Buschle et al.

(10) Patent No.: US 12,685,431 B2
(45) Date of Patent: Jul. 21, 2026

(54) METHOD FOR CALIBRATING A MEDICAL IMAGING DEVICE AND MEDICAL IMAGING DEVICE

(71) Applicant: KARL STORZ SE & Co. KG, Tuttlingen (DE)

(72) Inventors: Lukas Buschle, Tuttlingen (DE); Johannes Fallert, Tuttlingen (DE); Werner Göbel, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 326 days.

(21) Appl. No.: 18/256,343

(22) PCT Filed: Dec. 7, 2021

(86) PCT No.: PCT/EP2021/084577
§ 371 (c)(1),
(2) Date: Jun. 7, 2023

(87) PCT Pub. No.: WO2022/122725
PCT Pub. Date: Jun. 16, 2022

(65) Prior Publication Data
US 2024/0032773 A1 Feb. 1, 2024

(30) Foreign Application Priority Data

Dec. 8, 2020 (DE) ...................... 10 2020 132 564.9
Apr. 9, 2021 (DE) ...................... 10 2021 108 932.8

(51) Int. Cl.
A61B 1/00 (2006.01)
A61B 1/06 (2006.01)
H04N 23/50 (2023.01)

(52) U.S. Cl.
CPC ...... *A61B 1/00057* (2013.01); *A61B 1/00009* (2013.01); *A61B 1/00097* (2022.02); *A61B 1/0661* (2013.01); *H04N 23/555* (2023.01)

(58) Field of Classification Search
None
See application file for complete search history.

(56) References Cited

U.S. PATENT DOCUMENTS

2003/0210395 A1* 11/2003 Takahashi ............... G01J 3/462
356/405
2010/0039507 A1* 2/2010 Imade .................... H04N 23/56
382/128
(Continued)

FOREIGN PATENT DOCUMENTS

JP 2009273676 A 11/2009
JP 2010220794 A * 10/2010
(Continued)

OTHER PUBLICATIONS

International Preliminary Report on Patentability, Application No. PCT/EP2021/084577, dated Jun. 13, 2023.
(Continued)

*Primary Examiner* — Paul M Berardesca
(74) *Attorney, Agent, or Firm* — Brooks Kushman P.C.

(57) ABSTRACT

A method for calibrating a medical imaging device is provided. The medical imaging device may be an endoscope system or an exoscope system. The medical imaging device includes an optical system with optics and an imaging sensor for capturing an image of a viewing region, and image information of the image being subject to a spectral deviation as a result of an internal and/or external influence, as a result of the optical system, lighting and/or an ambient condition, said method having multiple steps. A medical
(Continued)

imaging device, in particular a medical endoscope or a medical exoscope incorporating the method is also provided.

15 Claims, 2 Drawing Sheets

(56)                    References Cited

U.S. PATENT DOCUMENTS

| | | | |
|---|---|---|---|
| 2014/0267657 A1* | 9/2014 | Takei | ..................... H04N 25/60 |
| | | | 348/68 |
| 2018/0299552 A1 | 10/2018 | Shu et al. | |
| 2019/0129037 A1 | 5/2019 | Fujita et al. | |

FOREIGN PATENT DOCUMENTS

| | | | |
|---|---|---|---|
| JP | 2013090884 A | 5/2013 | |
| JP | 2015134110 A | 7/2015 | |

OTHER PUBLICATIONS

International Search Report, Application No. PCT/EP2021/084577, mailed Apr. 4, 2022. ISA/European Patent Office.

* cited by examiner

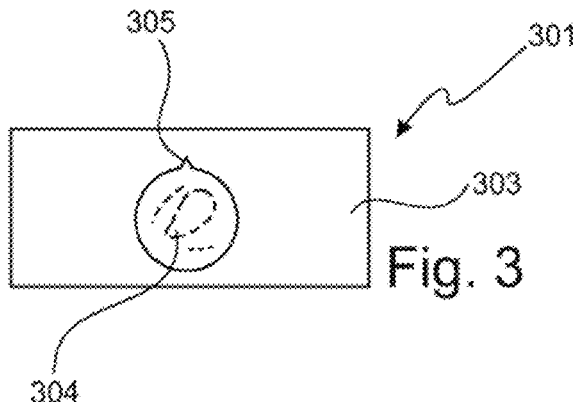
Fig. 3
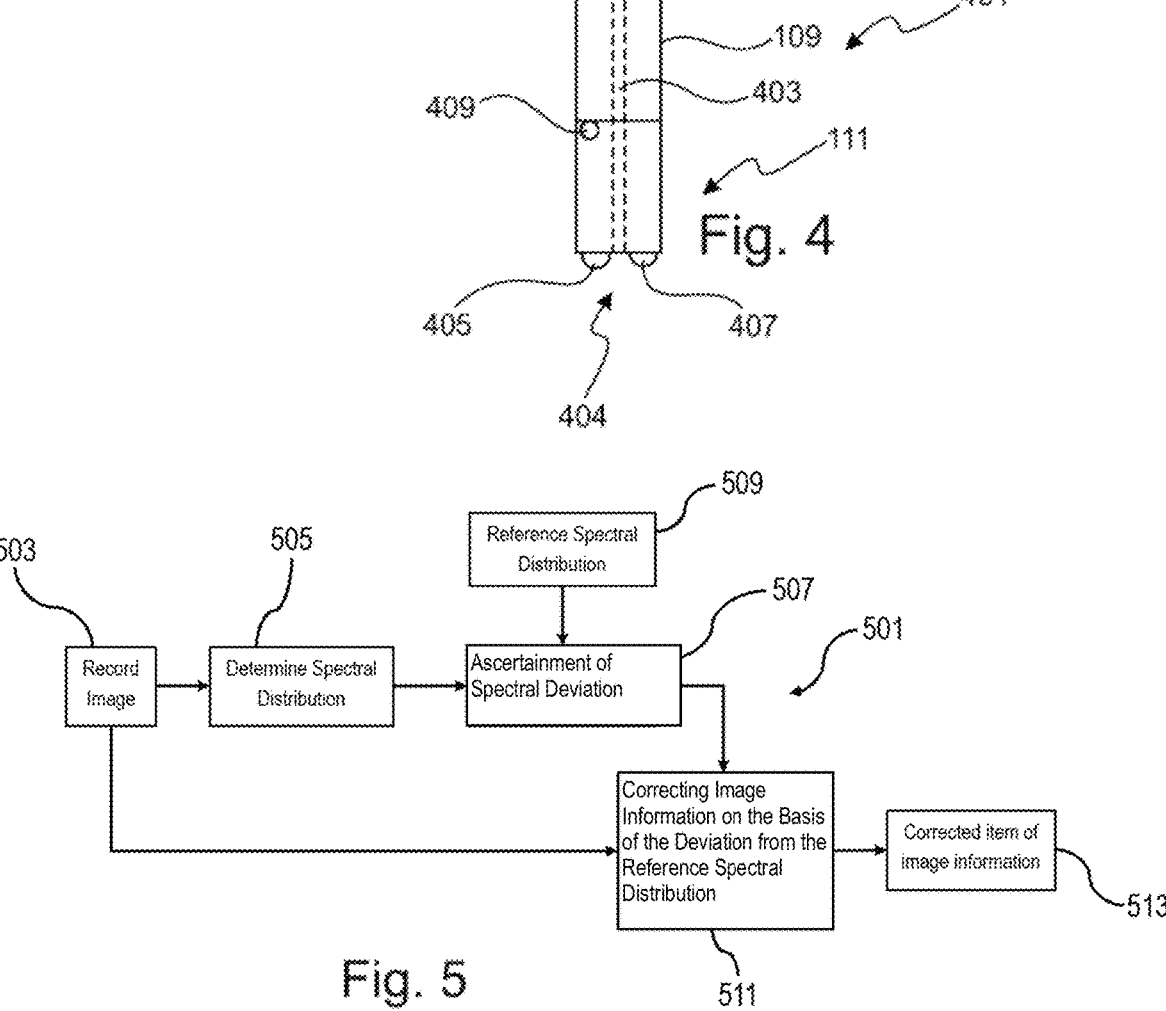
Fig. 4
Fig. 5

METHOD FOR CALIBRATING A MEDICAL IMAGING DEVICE AND MEDICAL IMAGING DEVICE

CROSS-REFERENCE TO RELATED APPLICATIONS

This application is the U.S. national stage of PCT/EP2021/084577 filed on Dec. 7, 2021, which claims priority of German Patent Application No. DE 10 2020 132 564.9 filed on Dec. 8, 2020, and German Patent Application No. DE 10 2021 108 932.8 filed on Apr. 9, 2021, the contents of which are incorporated herein.

TECHNICAL FIELD

The disclosure relates to a method for calibrating a medical imaging device, in particular an endoscope system or an exoscope system, wherein the imaging device includes an optical system having an optical unit and an image sensor for recording an image of an observation area and an item of image information of the image is subject to a spectral deviation due to an internal and/or external influence, in particular the optical system, lighting and/or an environmental condition, having multiple steps. Furthermore, the disclosure relates to a medical imaging device, in particular a medical endoscope or a medical exoscope.

BACKGROUND

Known medical imaging devices, such as endoscopes or exoscopes, are used both to record images under confined geometrical conditions and for analyzing certain parameters in an observation area. Inter alia, so-called hyperspectral or also multispectral imaging systems (HSI/MSI) for endoscopes or for exoscopes are known for this purpose.

Furthermore, diverse endoscopes are known in which a corresponding optical unit is designed to be rotatable at the tip of the respective endoscope. These can also be combined with HSI and/or MSI systems.

Moreover, it is typical, on endoscopes or exoscopes having a simple eyepiece for the observation with the human eye, to attach a camera to the eyepiece at the head of the respective device, so that an external display of the image of an observation area is enabled.

Known endoscopes or also exoscopes share the feature that in the event of a change of a distance to an observation area or to an observed object, such as an organ, and/or also due to the rotation of an optical system or an optical unit or, for example, an attached camera, a calibration required for a hyperspectral or multispectral imaging system is only present for a base position, and therefore if the described changes are carried out, a change of the image quality with respect to the ascertained results is produced, since the calibration is lost.

The object of the disclosure is to improve the prior art.

SUMMARY

The object is achieved by a method for calibrating a medical imaging device, in particular an endoscope system or an exoscope system, wherein the medical imaging device includes an optical system having an optical unit and an image sensor for recording an image of an observation area and an item of image information of the image is subject to a spectral deviation due to an internal and/or external influence, in particular due to the optical system, due to lighting and/or due to an environmental condition, having the following steps:

recording an item of image information of an image area, so that a first recording is present, determining a spectral distribution of the first recording, so that a spectral distribution of the first recording is present, ascertaining a spectral deviation on the basis of the spectral distribution of the first recording and a reference spectral distribution, so that a deviation from the reference spectral distribution is present, correcting the image information on the basis of the deviation from the reference spectral distribution, so that a corrected item of image information is present, so that the image information is prepared in such a way that the corrected image information is present with a reduced or eliminated spectral deviation.

By determining a spectral distribution of the first recording determined in a real usage environment, a corresponding spectral deviation from a reference spectral distribution can be ascertained. For each first recording, an item of information is thus present about the extent to which such a spectral distribution of the first recording deviates from a reference spectral distribution. The image information can then be corrected by this determined spectral deviation on the basis of this deviation from the reference spectral distribution, so that a corrected item of image information is present. The corrected image information is therefore compensated by the spectral deviation or recalibrated to the respective usage situation having changed parameters, so that a reduced or eliminated spectral deviation is present. In a respective usage environment, an accurate determination of, for example, tissue parameters by means of, for example, an MSI can thus take place, since the determination of these tissue parameters is dependent on a correspondingly accurate ascertainment of corresponding spectral distributions.

The following terms are explained at this point:

A "calibration" describes, in metrology or for a measurement process, a determination and/or documentation of a deviation of the respective measuring device in relation to another measuring device or a reference measure. The reference measure is also designated as a "normal" in this case. Such calibrating or such a calibration furthermore comprises a second step, namely a consideration of the ascertained deviation during a subsequent use of the respective measuring device for correcting the read-out values. A so-called calibrated measurement therefore supplies more accurate results or even exact results within a desired minimal deviation from the reality in relation to an uncalibrated measurement.

A "medical imaging device" is, for example, an endoscope, an endoscope system, or also an exoscope or exoscope system. Furthermore, such a medical imaging device can be any device which is suitable to be used with an imaging method in a medical environment, for example for ascertaining a corresponding image or also for determining parameters of an observed area. An endoscope is in this case a device using which, for example, an internal area of a human, for example an abdominal cavity, can be studied and parts therein can be manipulated. Such an endoscope comprises here, for example, both optical components and mechanical components for manipulating a correspondingly observed area or parts in this area. Reference is correctly made for this purpose to an endoscope system, wherein the "endoscope" designates the actual parts for image recording. However, these terms are often also used synonymously. An exoscope or also an exoscope system is in this case a comparable instrument for observing and/or manipulating exposed areas of an organism, for example a human during an open intervention. Tissue parameters or other parameters are determined here, for example, by means of a spectral analysis, often in consideration of correspondingly deliberately used lighting devices of special spectra. Thus, for example, an analysis via hyperspectral imaging (HSI) or multispectral imaging (MSI) can be carried out by means of such a medical imaging device.

An "optical system" can in this case be any device of the medical imaging device which is suitable or configured for recording, passing on and/or emitting items of image information or other items of optical information. Such an optical system, for example, guides light out of the observation area to an image sensor or image recording chip.

An "optical unit" describes here the entirety of optically conducting components. For example, such an optical unit includes lenses, light guides or corresponding filters, but also optical components additionally attached to an endoscope system.

An "image sensor" is, for example, a device or also a unit for electrically recording light-based items of information. For example, such an image sensor is a semiconductor-based component, which can record visible and also non-visible light. In general, such an image sensor can record any type of electromagnetic radiation if it is configured for a corresponding wavelength range. Such an image sensor is be arranged here, for example, at the tip, in a handle or a head of an endoscope or an exoscope, or also in an external camera attached to the endoscope system or exoscope system.

An "image" designates an image or a representation of a corresponding observation area, for example as colored pixels or the entirety of colored pixels or an electronic function respectively equivalent thereto. Such an image does not have to be physically present or visible for a human, but rather can also be present during processing or storage or preparation for a display for a human in electronic form and the items of information of a corresponding image comprise an observation area.

An "observation area" is in particular the area which is observed using the medical imaging device, for example such an observation area is an abdominal cavity, an organ or another component of an organism.

An "item of image information" is in this case the informative content of the described image, for example thus a corresponding number of pixels in corresponding color, an item of information about a corresponding spectral distribution of the respective image per pixel or also another item of meta-information, for example, of the respective image.

An "internal and/or external influence" describes any influence on the image information which changes or worsens the quality of the image information or an informative content of the image information and which is produced or caused in particular by the optical system, by lighting and/or by an environmental condition. Such an influence by the optical system can be, for example, an asymmetry of a corresponding lens, a filter effect of a filter or of an optical component which is unequal over an overall surface, or also in the simplest case soiling in the optical system. A corresponding influence by lighting is produced, for example, by an uneven spectral distribution of a corresponding light source which is used for the lighting. An environmental condition can be, for example, a corresponding background around the observation area, which accordingly corrupts reflected or scattered light, for example overlays it with a different color spectrum, or reflects or absorbs it, so that lighting intensity is changed.

"Lighting" is in this context in particular deliberate lighting of the observation area which is multispectral and/or carried out using a defined light spectrum, and which is then used, for example, for MSI or HSI imaging. A spectral deviation can also be caused here by this corresponding lighting, since deviations from the desired spectrum can also occur in the corresponding light spectra emitted by the lighting.

A "spectral deviation" can occur intentionally or unintentionally and is, for example, an unintentional filtering of a corresponding light spectrum, shading of certain spectral ranges or influencing of a corresponding spectral distribution in its intensity in corresponding spectral ranges. An intentional spectral deviation can thus also be generated, for example, in that lighting is carried out using corresponding lighting in order to provide an analysis of tissue parameters on the basis of a light spectrum then supplied to the image information. Such a spectral deviation can in particular be distributed inhomogeneously over multiple pixels or over all pixels of the image or also inhomogeneously over the entire image.

"Recording" an item of image information describes, for example, optically feeding the corresponding image information or an image corresponding thereto in the direction of the image sensor and converting the image information on the image sensor into, for example, an electronic signal.

A "recording" describes here a specific and identifiable image to be assigned of the corresponding image area in the observation area.

"Determining" a spectral distribution describes, for example, generating an item of information in such a way that a corresponding intensity of the respective light present in the recording is assigned to specific spectra or to specific frequencies of the light, so that a comprehensible item of information about a corresponding spectral distribution is present.

"Ascertaining" a spectral deviation describes comparing the spectral distribution to a respective recording having a reference spectral distribution, so that, for example, by means of a subtraction at corresponding frequencies, a respective item of information about a deviation in the intensity of the respective light incident at the frequency is present.

A "reference spectral distribution" describes here, for example, a spectral distribution established during the production or a quality control for a corresponding medical imaging device and assigned to the respective medical imaging device, which enables the most real possible imaging of an item of image information of the observation area. Such a reference spectral distribution is thus used, for example, as a "normal" in the meaning of a desired calibration. Such a reference spectral distribution is in particular distributed inhomogeneously and/or defined inhomogeneously over the image and enables a calibration corresponding to the inhomogeneity resulting therefrom. Therefore, a calibration with pixel accuracy can take place, for example in contrast to a white balance.

A "correction" of the image information describes a computer influence on the image information in such a way that the image information is corrected by means of the spectral deviation such that the image information is present corresponding to the reference spectral distribution of the medical imaging device. A result of such a correction is then, for example, the "corrected image information".

In order to be able to carry out the method advantageously in high-resolution imaging methods and for typical items of image information, the recording of an item of image information, the determination of a spectral distribution, the ascertainment of a spectral deviation and/or the correction of the image information is carried out for a pixel or for a respective pixel of the image and/or the image information.

As a result, for a respective pixel or, for example, also for all pixels of a corresponding image or a corresponding item of image information, a calibrated spectral distribution can be generated, so that a very accurate determination, for example of a tissue property by means of a multispectral analysis is also possible in high-resolution images having a large number of pixels.

A "pixel", which is also designated as an image point, image cell or image segment, designates individual color values or also brightness values of a digital raster graphic, as are typically used in electronic imaging methods. Such a pixel also designates here a corresponding surface element, for example of an image sensor, or also of a display screen, wherein a large number of pixels then result in a complete image.

BRIEF DESCRIPTION OF DRAWINGS

FIG. 3 shows a sectional detail with a corresponding image of the endoscope of FIG. 1, FIG. 4 shows an enlargement of the tip of the endoscope of FIG. 1 in a schematic side view, and FIG. 5 shows a method for calibrating corresponding images.

DETAILED DESCRIPTION OF PREFERRED EMBODIMENTS

Figure 1:
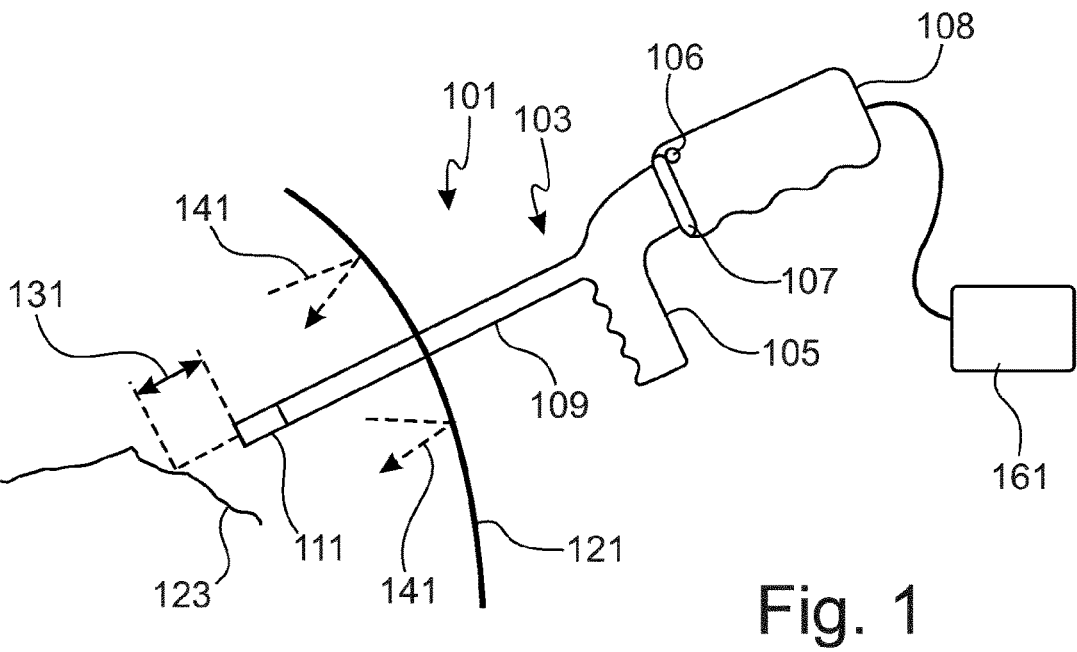
FIG. 1 shows an examination situation having an endoscope in a schematic side view, FIG. 2 a) to c) show a schematic representation of the rotation of an image with mathematical angle representation.

In one embodiment, the recording of an item of image information, the determination of a spectral distribution, the ascertainment of a spectral deviation and/or the correction of the image information takes place for one spectral range or multiple spectral ranges.

Using this procedure, it is made possible to perform a calibration as exactly as possible for the respective spectral range, so that, for example, a calibration can be carried out adapted to a multispectral analysis method for determining a tissue property.

A "spectral range" describes here, for example, a section from an overall spectrum of a corresponding spectral distribution.

For this purpose, in one embodiment, the image information is then corrected on the basis of the deviation from the reference spectral distribution for one spectral range or multiple spectral ranges, so that the image information is prepared in such a way that the corrected image information is present with a reduced or eliminated spectral deviation for a respective spectral range or multiple respective spectral ranges.

In a further embodiment, a distance from the observation area is ascertained and the reference spectral distribution is determined in dependence on this distance of the observation area, wherein the correction of the image information is carried out on the basis of the ascertained distance from the observation area.

By means of this distance, a calibration with respect to distance-dependent spectral deviations can thus take place. A distance to the observation area thus has the result, for example, that reflections from a background of the observation area result in a spectral deviation.

To ascertain this distance from the observation area reliably, the distance is determined by means of a laser, an ultrasound system and/or by means of an image evaluation.

Thus, for example, a laser interferometer, a laser distance meter or a unit for measuring a time-of-flight of a laser, also called "time-of-flight" analysis, can be used to ascertain the distance reliably and precisely. An ultrasound system can ascertain a corresponding distance via an echo time-of-flight, for example. Furthermore, it is possible to determine the distance by means of an image evaluation. For this purpose, a correlation or also a triangulation of corresponding items of image information takes place, for example in a stereo-endoscope, so that as a result the distance can be concluded.

In a further embodiment, the correction of the image information is carried out on the basis of an ascertained rotational position of the optical system and/or the optical unit.

Therefore, for example, in an endoscope or also exoscope having rotatable tip or having a rotatable camera attached to an eyepiece, a corresponding correction of the image information can be carried out in dependence on the rotational position. A corresponding calibration can therefore also be performed for each rotational position, which also takes place continuously and/or with pixel accuracy, for example. For this purpose, a correction in relation to a reference spectral distribution is carried out for each incremental rotational position.

A "rotational position" describes here, for example, a corresponding angle specification in relation to a zero angle or in relation to a starting position of the optical system and/or the optical unit. Thus, for example, the rotational position can be specified as an angle specification in "°". For each corresponding rotational position or for corresponding increments of rotational positions in relation to a full circle, a corresponding item of correction information can then be present in the form of a reference spectral distribution. In particular, a rotational position of the image sensor in relation to the optical system and/or in relation to the observation area is therefore designated.

In order to be able to ascertain the rotational position reliably without further components, the rotational position is ascertained on the basis of an optical indicator, assigned to the optical system and/or the optical unit, for the rotational position.

An image evaluation can thus be carried out, for example, in such a way that an anomaly or geometric deviation of a corresponding image, which is to be assigned to an angle position, is used to establish the rotational position.

An "optical indicator" can be, for example, a detail of an otherwise circular image surface, a marking, a point or another geometrical formation in the optical system and/or in the optical unit, which can be recognized by the image sensor and/or the components connected thereon such as of a display instrument having evaluation technology. Furthermore, a deviation or quality deviation generated in manufacturing of a corresponding medical imaging device can also be used as an optical indicator. Alternatively or additionally, an optical indicator can also be generated by reference image points of an image evaluation, if they are present in the image in dependence on the rotation.

Alternatively or also to create a redundancy, the rotational position is ascertained on the basis of a sensor.

A "sensor", which is also called a "measuring probe", is a technical component which can qualitatively and/or quantitatively detect physical or chemical properties and/or also material properties or qualities in its respective environment. For example, a corresponding electronic signal is then generated, which can be passed on and/or processed.

The rotational position can be ascertained here on the basis of a magnetic sensor, a Hall sensor, a laser sensor, a light sensor and/or an incremental encoder.

A "magnetic sensor" can be any sensor which uses magnetic properties to detect the rotational position. For example, such a magnetic sensor comprises a magnetized ring which is scanned by a magnetic pickup and thus ascertains a rotational position.

Such a magnetic sensor can also be embodied as a "Hall sensor", which can determine magnetic fields by means of the so-called Hall effect. A corresponding magnetic component of the optical system and/or the optical unit can thus be positioned opposite to a corresponding Hall sensor and a change of the rotational position of the optical system and/or the optical unit can result in a signal change at the Hall sensor.

A "laser sensor" can be any sensor which generates a measurement signal by means of a laser beam or the use of a laser beam. For example, such a laser sensor can scan a peripheral optical marking on the optical system and/or on the optical unit, so that a signal with respect to the rotational position is generated.

A rotational position also be scanned correspondingly by means of a light sensor, wherein, for example, an image of an incremental ring or an incremental encoder is read out and evaluated accordingly.

In order to be able to evaluate tissue properties reliably and precisely by means of the medical imaging device, the corrected image information is evaluated for an HSI or an MSI. This is carried out in particular to determine properties of the observation area, in particular a hemoglobin content, a water content and/or an oxygen saturation, which can be established, for example, in the corresponding tissue.

In a further embodiment, the observation area is lighted using a light source, wherein the light source is in particular configured to light the observation area using a light spectrum corresponding to a spectral evaluation, in particular by means of an HSI or MSI.

In order to also be able to ensure a reliable operation of the medical imaging device in the absence of a corresponding reference spectral distribution for a special rotational position and/or a special distance, and/or to only have to ascertain an economic number of reference spectral distributions in the manufacturing process, the reference spectral distribution is ascertained by means of an interpolation from reference spectral distributions, in particular stored reference spectral distributions of a known distance or known distances and/or a known rotational position or known rotational positions.

Thus, for example, if a reference spectral distribution is present on the left side of the currently present rotational position and a further reference spectral distribution is present on the right side of the currently present rotational position, the currently present rotational position can be covered by means of the interpolation of a corresponding intermediate area and a calibration can be carried out in spite of a lack of reference spectral distribution for this currently present rotational position.

An "interpolation" describes here a mathematical procedure in which for existing discrete data, for example measured values, a continuous function is found which also depicts intermediate areas of the existing discrete data. The values present between the discrete data are therefore ascertained and supplemented in terms of an approximation, so that unknown intermediate values can accordingly be ascertained as precisely as possible.

In a further aspect, the object is achieved by a medical imaging device, in particular a medical endoscope system or a medical exoscope system, which is configured to carry out a method according to one or more of the above-described embodiments.

Such a medical imaging device can ascertain images and/or items of image information of the observation area reliably and accurately even if, for example, an optical system and/or an optical unit of the medical imaging device is subject to a rotation and/or a distance of the respective optical system and/or the respective optical unit to the observation area is changed.

For example, such an endoscope system is an optical endoscope having an eyepiece and a camera attached to the eyepiece having, for example, a rotational angle sensor for determining a rotational position of the camera in relation to the optical system of the optical endoscope.

The disclosure is explained in more detail hereinafter on the basis of exemplary embodiments.

An examination situation 101 shows an endoscope 103. The endoscope 103 has a handle 105 for the grasping and operating of the endoscope 103 by an operator and an eyepiece 107 for the view for the operator. A camera 108 is attached to the endoscope 103 at the eyepiece 107, so that an image actually visibly prepared for the operator in the eyepiece 107 is recorded by means of the camera 108. Furthermore, the endoscope 103 includes a shaft 109 having a tip 111. By means of the endoscope 103, an organ 123 is observed within an abdominal wall 121 and an image of the organ 123 is generated and recorded by the camera 108 from the eyepiece 107. The tip 111 of the endoscope 103 is arranged here at a distance 131 from the organ 123. A rotational sensor 106, which is an optical incremental encoder, ascertains a rotation of the camera 108 in relation to the eyepiece 107.

The endoscope 103 furthermore includes units for lighting the organ 123, so that the organ is visible and reflections 141 also arise within the abdominal wall 121 as a side effect. These reflections 141 corrupt the image recorded by the endoscope 103 and fed to the observer.

Furthermore, the endoscope 103 includes an evaluation unit 161, on which both the image of the organ 123 recorded using the camera 108 and additional items of information are displayed. Thus, by means of the evaluation unit 161, in addition to the image of the organ 123, a superimposed image of a multispectral imaging (MSI) recording can be shown, accordingly perfusion values or also oxygen saturation values of the organ 123 can be displayed.

An image 201 represents a corresponding recording of the organ 123. The image 201 includes a circular edge 203 and an indicator 205 assigned to a zero radius 251. Furthermore, the image 201 includes an axis of rotation 211. An image surface 207 and an image surface 209 are shown here by way of example, which include spectral corruptions due to the reflections 141.

If the image 201 is rotated from the alignment on the zero radius 251 to the rotational radius 252 by a rotational angle 253, thus, for example, the image surfaces 207 and 209 shown by way of example also travel rotationally with the image 201. Furthermore, a shift of the axis of rotation 211 can occur in the image 201 due to precession. The cause of this is, for example, an off-center arrangement of a corresponding axis of rotation of the camera 108 in relation to the eyepiece 107.

Figure 2:
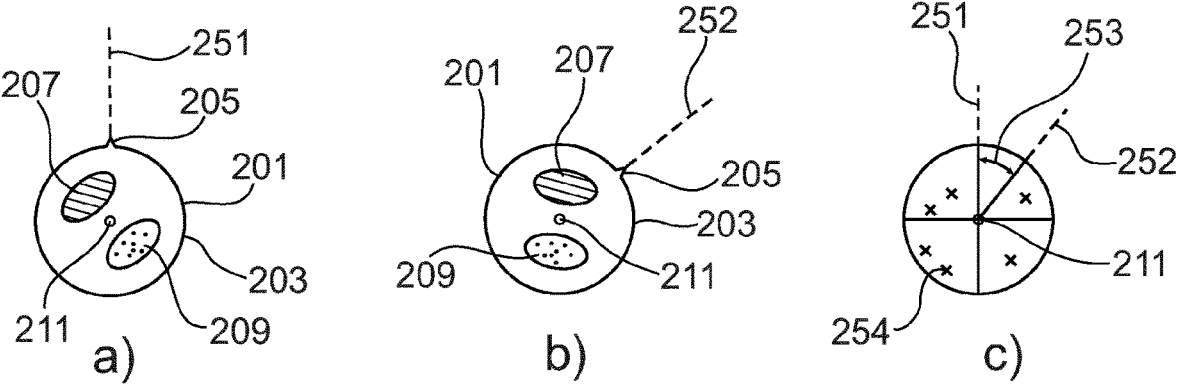

If the image 201 is rotated from the alignment on the zero radius 251 to an alignment to the rotational radius 252 by the rotational angle 253, reference points 254 in the image 201 shown by way of example thus also travel correspondingly (cf. FIG. 2c)). On the basis of these reference points, which depict, for example, significant color differences or contrast differences, the rotational angle 253 is determined by means of an image evaluation.

In an alternative, the rotational angle 253 can be determined on the basis of an image evaluation of the indicator 205, this can also take place redundantly to the determination of the rotational angle 253 by means of the reference points 254. In a further alternative, which can also be used redundantly with the image evaluation and/or the image evaluation of the indicator 205, the rotational angle 253 is ascertained by means of the rotation sensor 106.

A view detail 301 having a background 303 shows a possible representation on the evaluation unit 161. By way of example, an image 304 is shown here which contains both an optical image and superimposed items of color information with respect to a multispectral imaging. A corner 305 of the image 304 is used here as an indicator for a rotational position, by which a rotational angle of the image 304 is determinable analogously to the rotational angle 253.

An enlargement 401 of the endoscope 103 shows, in addition to a part of the shaft 109 and the tip 111, an image guide 403. By means of the image guide 403, the image of the organ 123 is passed on and converted in the endoscope 103 into a visible image. This visible image can then be displayed by means of the eyepiece 107 and the camera 108 on the evaluation unit 161. Furthermore, lighting 405 is arranged at an end area 404 of the tip 111. The lighting 405 is multispectral lighting here, so that individual spectral ranges can deliberately be generated to light the organ 123. It is thus possible to establish tissue properties by means of a spectral evaluation.

Furthermore, the tip 111 includes a laser sensor 407 for determining the distance 131.

In an alternative, the tip of a respective endoscope 103 or exoscope can also be rotatable, for example if an integrated image recorder is used in the endoscope instead of the camera 108. A rotational sensor 409 scans an incremental ring (not shown) on the shaft 109 of the endoscope 103 in this case. The rotational angle 253 can be determined by means of the rotational sensor 409 alternatively or redundantly to the described image evaluation.

Therefore, in the examination situation 101, both the distance 131 to the organ 123 and the rotational angle 253 are ascertainable reliably and accurately on the endoscope 103 in dependence on the camera 108 or alternatively or additionally on the tip 111.

A corresponding method 501 for calibrating the endoscope 103 will be described in detail as follows:

A recording 503 of an image of the organ 123 takes place at the distance 131 with the rotational angle 253. A corrupted image of the organ 123 is thus present. A determination 505 of the spectral distribution of this recorded image information then takes place, so that the spectral distribution is present for the further evaluation. This spectral distribution is fed to an ascertainment 507 of a spectral deviation. The ascertainment 507 makes use here of a reference spectral distribution 509, wherein the image information is corrected 511 on the basis of the deviation from the reference spectral distribution and the correction is ascertained by means of a subtraction. The deviation is the deviation of the determined spectral distribution from the reference spectral distribution here.

A superposition of the deviation of the reference spectral distribution with the originally recorded image information then takes place in such a way that a corrected item of image information 513 is generated. The corrected image information 513 contains the recorded image information here, wherein the spectral distribution is adapted in such a way that it corresponds to the real spectral distribution of the image information of the organ 123. An exact evaluation of the image information and display on the evaluation unit 161 can therefore take place on the basis of this calibrated measurement using the corrected image information.

The invention claimed is:

1. A method for calibrating a medical imaging device, the medical imaging device being one of an endoscope system or an exoscope system, wherein the medical imaging device includes an optical system having an optical unit and an image sensor for recording an image of an observation area and an item of image information of the image is subject to a spectral deviation due to an internal and/or external influence due to the optical system, a lighting and/or an environmental condition, the method having the following steps:

recording an item of image information of an image area, so that a first recording is present, determining a spectral distribution of the first recording, so that a spectral distribution of the first recording is present, ascertaining a spectral deviation on the basis of the spectral distribution of the first recording and a reference spectral distribution, so that a deviation from the reference spectral distribution is present, wherein a distance from the observation area is ascertained and the reference spectral distribution is determined in dependence on this distance from the observation area, correcting the image information on the basis of the deviation from the reference spectral distribution, so that a corrected item of image information is present, wherein the correction of the image information is carried out on the basis of the ascertained distance from the observation area, so that the image information is prepared in such a way that the corrected image information is present with a reduced or eliminated spectral deviation.

2. The method as set forth in claim 1, wherein the recording of an item of image information, the determination of a spectral distribution, the ascertainment of a spectral deviation and/or the correction of the image information is carried out for a pixel or for a respective pixel of the image and/or the image information.

3. The method as set forth in claim 1, wherein the recording of an item of image information, the determination of a spectral distribution, the ascertainment of a spectral deviation and/or the correction of the image information takes place for one spectral range or multiple spectral ranges.

4. The method as set forth in claim 3, wherein a correction of the image information takes place on the basis of the deviation from the reference spectral distribution for one spectral range or multiple spectral ranges, so that the image information is prepared in such a way that the corrected image information is present with a reduced or eliminated spectral deviation for one respective spectral range or multiple respective spectral ranges.

5. The method as set forth in claim 1, wherein the ascertained distance is determined by means of a laser, an ultrasound system and/or by means of an image evaluation.

6. The method as set forth in claim 1, wherein the correction of the image information is carried out on the basis of an ascertained rotational position of the optical system and/or the optical unit.

7. The method as set forth in claim 6, wherein the rotational position is ascertained on the basis of an optical indicator, assigned to the optical system and/or the optical unit, for the rotational position.

8. The method as set forth in claim 7, wherein the rotational position is ascertained by means of an image evaluation to recognize the optical indicator for the rotational position.

9. The method as set forth in claim 6, wherein the rotational position is ascertained on the basis of a sensor.

10. The method as set forth in claim 9, wherein the rotational position is ascertained on the basis of a magnetic sensor, a Hall sensor, a laser sensor, a light sensor and/or an incremental encoder.

11. The method as set forth in claim 1, wherein the corrected image information is evaluated for an HSI or an MSI, in particular for determining properties of the observation area, in particular a hemoglobin content, a water content and/or an oxygen saturation.

12. The method as set forth in claim 1, wherein the observation area is lighted using a light source, wherein the light source is configured in particular to light the observation area using a light spectrum corresponding to a spectral evaluation, in particular by means of an HSI or an MSI.

13. A medical imaging device, the medical imaging device being one of a medical endoscope system or medical exoscope system, configured to carry out a method as set forth in claim 1.

14. A method for calibrating a medical imaging device, the medical imaging device being one of an endoscope system or an exoscope system, wherein the medical imaging device includes an optical system having an optical unit and an image sensor for recording an image of an observation area and an item of image information of the image is subject to a spectral deviation due to an internal and/or external influence due to the optical system, a lighting and/or an environmental condition, the method having the following steps:

recording an item of image information of an image area, so that a first recording is present, determining a spectral distribution of the first recording, so that a spectral distribution of the first recording is present, ascertaining a spectral deviation on the basis of the spectral distribution of the first recording and a reference spectral distribution, so that a deviation from the reference spectral distribution is present, correcting the image information on the basis of the deviation from the reference spectral distribution, so that a corrected item of image information is present, wherein the correction of the image information is carried out on the basis of an ascertained rotational position of the optical system and/or the optical unit, so that the image information is prepared in such a way that the corrected image information is present with a reduced or eliminated spectral deviation.

15. A method for calibrating a medical imaging device, the medical imaging device being one of an endoscope system or an exoscope system, wherein the medical imaging device includes an optical system having an optical unit and an image sensor for recording an image of an observation area and an item of image information of the image is subject to a spectral deviation due to an internal and/or external influence due to the optical system, a lighting and/or an environmental condition, the method having the following steps:

recording an item of image information of an image area, so that a first recording is present, determining a spectral distribution of the first recording, so that a spectral distribution of the first recording is present, ascertaining a spectral deviation on the basis of the spectral distribution of the first recording and a reference spectral distribution, so that a deviation from the reference spectral distribution is present, wherein the reference spectral distribution is ascertained by means of an interpolation from reference spectral distributions, in particular stored reference spectral distributions of a known distance or known distances and/or a known rotational position or known rotational positions, correcting the image information on the basis of the deviation from the reference spectral distribution, so that a corrected item of image information is present, so that the image information is prepared in such a way that the corrected image information is present with a reduced or eliminated spectral deviation.

* * * * *